United States Patent
Ten Kate (10) Patent No.: US 10,854,063 B2
(45) Date of Patent: Dec. 1, 2020

(54) DETECTING PERIODS OF INACTIVITY

(71) Applicant: KONINKLIJKE PHILIPS N.V., Eindhoven (NL)

(72) Inventor: Warner Rudolph Theophile Ten Kate, Waalre (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/609,482

(22) PCT Filed: Apr. 23, 2018

(86) PCT No.: PCT/EP2018/060277
§ 371 (c)(1),
(2) Date: Oct. 30, 2019

(87) PCT Pub. No.: WO2018/202451
PCT Pub. Date: Nov. 8, 2018

(65) Prior Publication Data
US 2020/0066130 A1    Feb. 27, 2020

(30) Foreign Application Priority Data
May 2, 2017  (EP) ..................................... 17169013

(51) Int. Cl.
*G08B 21/04* (2006.01)
*G06F 3/01* (2006.01)
(Continued)

(52) U.S. Cl.
CPC .......... *G08B 21/0415* (2013.01); *G06F 3/011* (2013.01); *G06F 3/017* (2013.01); *G06F 9/542* (2013.01); *G08B 21/06* (2013.01)

(58) Field of Classification Search
None
See application file for complete search history.

(56) References Cited

U.S. PATENT DOCUMENTS

| | | | |
|---|---|---|---|
| 5,296,707 A | 3/1994 | Nozu | |
| 6,881,957 B2 | 4/2005 | Dougherty et al. | |

(Continued)

FOREIGN PATENT DOCUMENTS

| | | | |
|---|---|---|---|
| GB | 2348725 A | 10/2000 | |
| WO | 2013014578 A1 | 1/2013 | |
| WO | 2014029922 A1 | 2/2014 | |

OTHER PUBLICATIONS

International Search Report and Written Opinion, International Application No. PCT/EP2018/060277, dated Jul. 17, 2018.

(Continued)

*Primary Examiner* — Fekadeselassie Girma (57) ABSTRACT

Techniques are described herein for monitoring activities of organisms, including sleep. In various embodiments, logic (116) may receive, from a first sensor (106) adapted to detect activity in a first area (104), signal(s) indicating activity of an organism. Based on these signal(s), the logic may identify (504) a first time at which the organism transitions into a first state. The logic may later receive (508), from a second sensor (110, 114) adapted to detect activity in a second area (108, 112), signal(s) indicative of activity in the second area. Based on these subsequent signal(s), the logic may identify (510) a second time that is after the first time, determine (512) whether the first sensor provided signal(s) indicative of activity in the first area within another time interval preceding the second time, and selectively store (514) an indication of transition of the organism into a second state based on the determination.

15 Claims, 6 Drawing Sheets

(51) Int. Cl.
G06F 9/54 (2006.01)
G08B 21/06 (2006.01)

(56) References Cited

U.S. PATENT DOCUMENTS

| | | | |
|---|---|---|---|
| 7,764,167 B2 | 7/2010 | Reeves et al. | |
| 8,461,988 B2 | 6/2013 | Tran | |
| 8,901,476 B2* | 12/2014 | O'Shea | G08B 21/18 |
| | | | 250/221 |
| 9,529,437 B2* | 12/2016 | Kahn | G06F 3/017 |
| 9,530,080 B2* | 12/2016 | Glazer | H04N 5/2251 |
| 9,551,804 B1* | 1/2017 | Kechichian | A61B 5/1117 |
| 9,993,166 B1* | 6/2018 | Johnson | A61B 5/0022 |
| 10,447,972 B2* | 10/2019 | Patil | G06T 7/246 |
| 10,593,184 B2* | 3/2020 | Greene | G06K 9/00718 |
| 10,708,550 B2* | 7/2020 | Glazer | G06K 9/00335 |
| 2005/0137465 A1 | 6/2005 | Cuddihy et al. | |
| 2010/0007502 A1 | 1/2010 | Noury et al. | |
| 2010/0081411 A1* | 4/2010 | Montenero | G08B 21/0233 |
| | | | 455/404.2 |
| 2011/0140913 A1* | 6/2011 | Montenero | G08B 21/0233 |
| | | | 340/870.07 |
| 2015/0028113 A1* | 1/2015 | Day | F24F 11/30 |
| | | | 236/51 |
| 2015/0102226 A1* | 4/2015 | Monaci | G01J 1/4228 |
| | | | 250/347 |
| 2015/0305689 A1* | 10/2015 | Gourmelon | A61B 5/002 |
| | | | 600/301 |
| 2017/0056665 A1* | 3/2017 | Kane | A61N 1/36542 |
| 2017/0119283 A1* | 5/2017 | Ten Kate | A61B 5/6801 |
| 2017/0123516 A1* | 5/2017 | Li | G08C 23/04 |
| 2017/0139471 A1* | 5/2017 | Bury | G01P 13/00 |
| 2018/0000408 A1* | 1/2018 | Heinrich | A61B 5/113 |
| 2018/0000414 A1* | 1/2018 | Lowet | A61B 5/7271 |
| 2018/0326173 A1* | 11/2018 | Ewers | A61M 16/205 |
| 2019/0278339 A1* | 9/2019 | Cooper | G06F 1/1618 |
| 2020/0000441 A1* | 1/2020 | Lafon | A61B 5/01 |
| 2020/0129727 A1* | 4/2020 | Lazarovich | A61B 5/4809 |
| 2020/0178887 A1* | 6/2020 | Correa Ramirez | A61B 5/4806 |

OTHER PUBLICATIONS

Hayes, T. et al., "Estimation of Rest-Activity Patterns using Motion Sensors", 32nd Annual International Conference of the IEEE EMBS, Buenos Aires, Argentina, Aug. 31-Sep. 4, 2010.

Zappi, P. et al., "Tracking Motion Direction and Distance With Pyroelectric IR Sensors", IEEE Sensors Journal, vol. 10, No. 9, Sep. 2010.

* cited by examiner

DETECTING PERIODS OF INACTIVITY

CROSS-REFERENCE TO PRIOR APPLICATIONS

This application is the U.S. National Phase application under 35 U.S.C. § 371 of International Application No. PCT/EP2018/060277, filed on 23 Apr. 2018, which claims the benefit of European Patent Application No. 17169013.4, filed on 2 May 2017. These applications are hereby incorporated by reference herein.

TECHNICAL FIELD

Various embodiments described herein are directed generally to health care. More particularly, but not exclusively, various methods, apparatus and systems disclosed herein relate to detecting periods of inactivity (e.g., sleep) of organisms/subjects such as patients in particular areas and drawing conclusions about states of the organisms based on the detected inactivity.

BACKGROUND

There are a variety of scenarios in which it is useful to detect activity/inactivity of organisms, for instance mammals, subjects (e.g., users, patients), in particular areas to draw conclusions about states of those organisms. For example, medical personnel may determine that for some subjects, e.g., elderly patients, independent and/or unsupervised living is not acceptable. Consequently, the subjects' homes may be equipped with a variety of sensors, including presence sensors, motion sensors, sensors that detect physiological parameters, power sensors, humidity sensors, carbon-dioxide sensors, temperature sensors, light sensors, pressure mats, weight scales, cameras, open-close sensors that detect opening and/or closing of doors, windows, appliances such as refrigerators, etc., that can be used to monitor one or more aspects of the subjects' wellbeing. For example, such sensors can be used to assess the sensed subject activity of daily life (ADL), for instance to determine whether the subject spends an inordinate amount of time in an area such as the restroom, to monitor how often a subject visits the toilet, to determine whether a subject visits the toilet at unusual times, etc.

Among other aspects about the organism (hereinafter, "subject") that may be important to monitor, sleep is often assessed as of particular relevance. Techniques exist that employ sensors such as passive infrared ("PIR") sensors, light sensors, camera sensors, pressure mats (e.g., configured to detect the subject's mass or weight, and hence, bed occupancy), and so forth, to monitor sleep behavior. However, at least some of these techniques may have various shortcomings. For example, pressure mats may be prone to shifting position in the bed, so that the subject may not necessarily be laying on the pressure mat when sleeping. Additionally, pressure mats tend to be relatively high maintenance (they may require frequently adjustment and/or recalibration whenever the bed is cleaned) and expensive. While it is possible to deploy arrays of light or PIR sensors, e.g., as a vertical stack that detects (among other things) movement, such as beneath the bed, this approach may not be sufficiently sensitive and may be prohibitively expensive. Additionally, these techniques also fail to account for situations in which a subject is not alone in their residence. For example, many subjects may have pets. Pet movement can trigger various motion sensors to provide spurious signals that can cause errors when attempting to monitor sleep behavior. Such errors may also be caused by visitors to the subject's residence (e.g., family, medical personnel, etc.).

It is therefore a drawback of known monitoring system that sleeping pattern and/or behavior cannot be unobtrusively and effectively assessed for remote monitoring purposes.

WO 2013/014578 discloses a monitoring system for monitoring a monitored area, comprising at least three sensors, each configured to detect the presence or absence of a subject in a predetermined horizontal sensor area and to generate a sensor signal.

SUMMARY

There is consequently a need to accurately and unobtrusively monitor subjects in their living environment such as to infer conclusion on such subjects activity/inactivity, and more particularly to detect sleeping pattern and/or behavior of said subject.

The invention is defined by the claims.

The present disclosure is directed to methods systems and apparatus for detecting activity/inactivity of organisms such as elderly subjects in particular areas and drawing conclusions about states of the organisms based on the detected activity/inactivity. For example, one or more sensors may be provided in a subject's bedroom and may be adapted to detect activity in and/or near the subject's bed. In some embodiments, when activity is detected in the subject's bed and then that detected activity ceases, it may be presumed that the subject has gone to sleep.

However, additional detected activity in the bed does not necessarily imply that the subject is awake because people (and more generally, organisms) tend to move around somewhat while sleeping. To determine when the subject has truly awoken, e.g., to go to the bathroom, get a drink in the kitchen, or simply to start their day, some techniques described herein may rely on additional activity detected outside of the bedroom to effectively corroborate activity detected in the bedroom. For example, in some embodiments, one or more additional sensors may be deployed elsewhere in the subject's residence, e.g., outside of the bedroom (for instance, in the kitchen, in the bathroom, in the living room, in the toilet, in the hallway, etc.), in an area of the bedroom that is distinct from the bed, etc. Of course, activity outside of the bedroom might not necessarily be caused by the subject. Pets and/or visitors can also trigger sensors deployed outside of the bedroom while the subject remains asleep. Accordingly, techniques are also described herein for disregarding outside-of-the-bedroom movement caused by organism(s) other than the subject being monitored.

As used herein, a "sensor" can be any sensor that provides a signal indicative of detected activity (e.g., motion) of an individual. This indication includes a level of the activity. For example, a binary level would be a sensor that is triggered in response to a minimum amount of motion. An 'ON' flag is signaled when motion above a minimum level is detected, and an 'OFF' flag is signaled when that motion ceases back below that or another threshold. A sensor may include a variety of different sensors types, such as conventional motion sensors, presence sensors, door opening sensors that raise signals when a door such as a refrigerator door, a microwave door, a cabinet door, a door between rooms, etc., is opened or closed, pressure mats, digital cameras, sonar sensors, sound sensors, and so forth.

In some embodiments, a "signal indicative of detected activity" can indicate motion, directly or indirectly. In the case of conventional motion sensors (and some presence sensors that rely on detected motion), the signal directly corresponds to detected motion, and thus is directly indicative of detected motion. For example, a motion sensor may provide a signal having a first value (e.g., on) while motion is detected and a second value (e.g., off) while motion is not detected. Other sensors may raise signals that are indirectly indicative of motion. Indeed with some sensors, a signal indicative of detected motion corresponds to a change (e.g., delta) in what the sensor detects, rather than to detected motion directly. For example, a pressure mat may detect presence so long as a person is on top of it, regardless of whether the person is actually moving. However, when the person first mounts the pressure mat, dismounts from the pressure mat, or moves around sufficiently on the pressure mat, there will be a change in what the pressure mat detects. This change will be evident in the signal produced by the pressure mat, and hence, the signal produced by the pressure mat is indicative of detected motion. The same goes for presence sensors that do not rely on movement to detect presence. For example, some presence sensors may raise a signal indicative of presence so long as body heat, a human form, etc., are detected, regardless of whether the subject is moving. However, when the organism moves, especially in or out of the presence sensor's field of view, a corresponding change in the signal provided by the presence detector is indicative of detected movement.

Generally, in one aspect, a method may include: receiving, by logic communicatively coupled with a first sensor that is adapted to detect activity in a first area, the first area comprising a sleeping area, a first set of one or more signals indicative of detected activity of an organism in the first area; identifying, by the logic, based on the first set of one or more signals received from the first sensor, a first point in time after cessation of the detected activity within the first area by a predetermined time interval; storing, by the logic based on the identifying, a first indication that signifies a transition of the organism into a first state at the first point in time, wherein the first state is a sleep state; receiving, by the logic from a second sensor that is communicatively coupled with the logic and adapted to detect activity in a second area that is different than the first area, a second set of one or more signals indicative of activity within the second area; identifying, by the logic, based on the one or more signals received from the second sensor, a second point in time that is after the first point in time; determining, by the logic, whether the first sensor provided any signals indicative of activity detected in the first area within a second time interval immediately preceding the second point in time; if the first sensor provided any signals indicative of activity detected in the first area within the second time interval immediately preceding the second point in time, storing (by the logic, a second indication that signifies a transition of the organism into a second state, wherein the second state is an awake state; and if the first sensor did not provide any signals indicative of activity detected in the first area within the second time interval immediately preceding the second point in time, refraining from storing, by the logic, the second indication that signifies a transition of the organism into a second state.

In various embodiments, the first sensor comprises a passive infrared sensor, a light sensor, or a door opening sensor. In various embodiments, the one or more signals received from the first sensor include a first signal indicative of motion detected in the first area and a second signal indicative of cessation of motion in the first area. In various embodiments, the second sensor is integral with a kitchen appliance.

In various embodiments, the first area comprises a bed. In various embodiments, the refraining includes disregarding or discarding, by the logic, the one or more signals received from the second sensor. In various embodiments, the second sensor is integral with a heating ventilation and air conditioning ("HVAC") appliance. In various embodiments, the second sensor is integral with a luminaire.

The techniques described herein provide a variety of (technical) advantages. For example, in some embodiments, techniques described herein may account for spurious sensor signals triggered by organisms other than a subject being monitored for inactivity. By accounting for (e.g., discarding, ignoring) these spurious sensor signals, it is possible to ascertain periods of sleep of a subject more accurately than was possible using conventional techniques. This increased accuracy enables, for instance, medical personnel to better treat subjects (e.g., patients) who may or may not have trouble sleeping. By contrast, failing to account for spurious sensor signals, as was the case with conventional techniques, may raise "false positives" indicating that the subject was awake, which in turn may result in medical personnel providing unnecessary and potentially counterproductive treatments to an organism that was in fact getting sufficient sleep.

Another advantage provided by techniques described herein is the ability to leverage presence and/or motion sensors that are already commonplace to determine periods of inactivity of a subject. As will be described below, signals from a variety of motion and/or presence sensors that may already be deployed in a subject's residence, such as motion/presence sensors integral with smart luminaires, smart appliances, etc., may be "commandeered" for purposes of performing techniques described herein. This reduces costs and/or maintenance relative to conventional techniques, which typically required installation of equipment such as specialized sensors (e.g. infrared sensors (for instance PIR sensors), light sensors) and/or pressure mats.

In another aspect, there is provided a computer program product comprising a computer readable medium having computer readable code embodied therein. The computer readable code being configured such that, on execution by a suitable computer or processor, the computer or processor is caused to perform a method in accordance with the embodiments of the present disclosure.

In a yet other aspect, there is provided an apparatus for determining one or more period of inactivity of a subject. In one embodiment, said apparatus comprises a processor configured to receive a first set of one or more signals indicative of detected activity of a subject in a first area, the first area comprising a sleeping area. The processor is further configured to identify, based on the first set of one or more signals, a first point in time after cessation of the detected activity in the first area by a predetermined time interval. The processor is further configured to store, based on the identification, a first indication that signifies a transition of the subject into a first state, wherein the first state is a sleep state. The processor is further configured to receive a second set of one or more signals indicative of activity in a second area that is different than the first area. The processor is further configured to identify, based on the second set of one or more signals, a second point in time that is after the first point in time. The processor is further configured to determine whether the first set of signals provided any signals indicative of activity detected in the first area within a second time interval immediately preceding the second point in time; if the first set of signals provided any signals indicative of activity detected in the first area within the second time interval immediately preceding the second point in time, store a second indication that signifies a transition of the subject into a second state, wherein the second state is an awake state; and if the first set of signals did not provide any signals indicative of activity detected in the first area within the second time interval immediately preceding the second point in time, refrain from storing the second indication that signifies a transition of the subject into a second state.

In a yet other aspect, there is provided a system for determining one or more periods of inactivity of a subject, wherein said system comprise a first, a second sensor and a processor. In an embodiment, the first sensor is adapted to detect activity in a first area, the first area comprising a sleeping area, and generate a first set of one or more signals indicative of detected activity of a subject within the first area. The second sensor is adapted to detect activity in a second area that is different than the first area, and to generate a second set of one or more signals indicative of activity within the second area. The processor is communicatively coupled to the first sensor and the second sensor, the processor being configured to: i) identify, based on the first set of one or more signals received from the first sensor, a first point in time after cessation of the detected activity in the first area by a predetermined time interval; ii) store, based on the identification, a first indication that signifies a transition of the subject into a first state, wherein the first state is a sleep state; iii) identify, based on the second set of one or more signals received from the second sensor, a second point in time that is after the first point in time; iv) determine whether the first sensor provided any signals indicative of activity detected in the first area within a second time interval immediately preceding the second point in time: a) if the first sensor provided any signals indicative of activity detected in the first area within the second time interval immediately preceding the second point in time, store a second indication that signifies a transition of the subject into a second state, wherein the second state is an awake state; and b) if the first sensor did not provide any signals indicative of activity detected in the first area within the second time interval immediately preceding the second point in time, refrain from storing the second indication that signifies a transition of the subject into a second state.

Advantages herein described apply for methods, as well as, with the necessary modifications, for apparatus and systems in accordance with the present disclosure, as further elucidated hereunder.

These and other aspects of the invention are apparent from and will be elucidated with reference to the embodiments described hereinafter.

It will be appreciated by those skilled in the art that two or more of the above-mentioned options, implementations, and/or aspects of the invention may be combined in any way deemed useful.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

In the drawings, like reference characters generally refer to the same parts throughout the different views. Also, the drawings are not necessarily to scale, emphasis instead generally being placed upon illustrating various principles of the embodiments described herein.

DETAILED DESCRIPTION

Certain embodiments will now be described in greater details with reference to the accompanying drawings. In the following description, like drawing reference numerals are used for like elements, even in different drawings. The matters defined in the description, such as detailed construction and elements, are provided to assist in a comprehensive understanding of the exemplary embodiments. Also, well-known functions or constructions are not described in detail since they would obscure the embodiments with unnecessary detail. Moreover, expressions such as "at least one of", when preceding a list of elements, modify the entire list of elements and do not modify the individual elements of the list.

There are a variety of scenarios in which it is useful to detect activity/inactivity of subjects in particular areas to draw conclusions about states of those subjects. For example, medical personnel may determine that for some subjects, e.g., elderly patients, independent living is not acceptable. Consequently, the subjects' homes may be equipped with a variety of sensors, including presence sensors, motion sensors, sensors that detect physiological parameters, etc., that can be used to monitor aspects of the subjects' wellbeing. However, signals raised by these various sensors may be erroneous if triggered by an organism other than a subject, such as a pet or visitor. Accordingly, there is a need to monitor organisms such as subjects unable to live independently in a manner that is insensitive to spurious sensor events. More particularly, there is a need to detect and/or track sleep behavior of subjects in a manner that is insensitive to spurious activity caused by other organisms. In view of the foregoing, various embodiments and implementations of the present disclosure are directed to using a plurality of sensors to detect activity/inactivity of subjects such as elderly patients in particular areas, and to draw conclusions about states of the subjects based on the detected activity/inactivity, while ignoring spurious sensor events.

Figure 1:
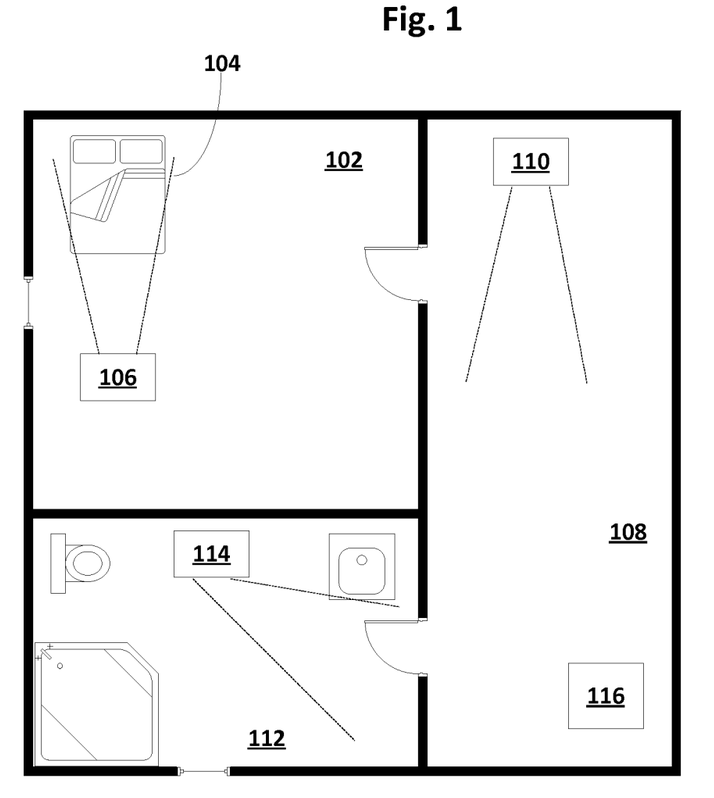
FIG. 1 illustrates an example environment in which techniques described herein may be implemented, in accordance with various embodiments.

FIG. 1 depicts an example environment in which techniques described herein may be practiced, in accordance with various embodiments. A bedroom 102 includes a bed 104 and a bed area sensor 106. Bed area sensor 106 may take various forms, such as a PIR-based motion sensor, a microwave-based motion sensor, an area reflective type motion sensor (e.g., light-emitting diode emits light and detects reflection), an ultrasonic-based motion sensor, a vibration-based motion sensor, a motion sensor that combines one or more of the aforementioned technologies, and so forth. In FIG. 1, bed area sensor 106 has a field of view that captures bed 104—as indicated by the dashed lines roughly indicating a field of view of bed area sensor 106—and therefore is configured to detect movement in and/or near bed 104.

Bedroom 102 opens into a hallway (or corridor) 108 in which what will be referred to as a "hallway" sensor 110 is mounted. Hallway sensor 110 may be the same type of sensor as bed area sensor 106, or a different type of sensor. In this example, hallway sensor 110 has a field of view—as indicated by the dashed lines—down a length of hallway 108. Accordingly, hallway sensor 110 is configured to detect activity in hallway 108. Hallway 108 leads into a bathroom 112 in which what will be referred to as a "bathroom" sensor 114 is mounted. As indicated by the dashed lines, bathroom sensor 114 has a field of view that is oriented towards the entrance into bathroom 112 from hallway 108. However, this is not meant to be limiting, and in other embodiments, bathroom sensor 114 may be positioned elsewhere in bathroom 112, e.g., at the door pointed towards the bathroom, at the toilet, and so forth. By pointing a field of view of bathroom sensor 114 towards a separate area from other sensors, such as hallway sensor 110, it may be possible to reduce and/or eliminate sensor crosstalk.

The sensors depicted in FIG. 1 are merely one example of a sensor layout that may be used to implement techniques described herein. One or more additional sensors may be further deployed, and in some cases only a single sensor is deployed outside of the bedroom (or within bedroom 102 but aimed away from bed 104, such as towards the entrance of bedroom 102). Sensors that are adapted to detect activity in areas other than bed 104, such as hallway sensor 110 and bathroom sensor 114, may be referred to herein as "other" sensors. As will be described in more detail below, in various embodiments, other sensors may be used to, among other things, corroborate that a person has left bed 104 and therefore is no longer sleeping, detect that the user is using the toilet, etc.

In various embodiments, sensors 106, 110, 114, etc. may be communicatively coupled with a control engine 116 (also referred to generally as "logic"). Control engine 116 may be configured to perform selected aspects of the present disclosure, including tracking periods of inactivity such as sleep. Control engine 116 may take various forms, such as one or more computing devices contained within and/or outside of the household/building that is configured to perform selected aspects of the present disclosure. In some embodiments, control engine 116 may take the form of an application-specific integrated circuit ("ASIC") or a field-programmable gate array ("FPGA"). In other embodiments, control engine 116 may include one or more processors and memory storing instructions that cause the one or more processors to perform selected aspects of the present disclosure. In various embodiments, the sensors may be communicatively coupled with control engine 116 and/or each other via one or more wired or wireless communication networks (not depicted) that employ various types of communication technologies, such as Wi-Fi, ZigBee, Z-wave, Bluetooth, Ethernet, etc. While control engine 116 is depicted in hallway 108, this is not meant to be limiting; control engine 116 may be deployed at any location within the building and/or outside of the building (e.g., on one or more servers forming what is commonly referred to as a "cloud" computing environment). In some embodiments, control engine 116 may act as a "gateway" between the residence and further processing. For example, control engine 116 may provide data it collects from sensors to one or more remote computing devices. Such remote computing devices may be maintain by, for instance, a health care provider that is monitoring the subject. In some embodiments, caregivers of the subject may have access to such remote computing devices so that they can view the subject's sleep behavior.

In some embodiments, various sensors described herein, especially other sensors outside of bedroom 102, may be integral with appliances that nominally serve other purposes, such heating ventilation and air conditioning ("HVAC"), entertainment, and/or lighting. For example, in some embodiments, hallway sensor 110 and/or bathroom sensor 114 may be integral with a so-called "smart" (e.g., networked) thermostat that dynamically and automatically adjusts temperature and/or other environmental settings (e.g., humidity) based on detected presence of one or more individuals. As another example, in some embodiments, hallway sensor 110 and/or bathroom sensor 114 may be integral with a so-called "smart" (e.g., networked) luminaire that is configured to dynamically select one or more properties of light it emits based on detected presence of one or more individuals. As yet another example, in some embodiments, one or more other sensors (e.g., a sensor in a living room) may be integral with a motion-sensing input device that nominally is used, for instance, to play video games on a television. Indeed, any activity sensor that is integral with any device, such as a smart phone, tablet computer, stand-alone interactive speaker, vehicle computing system, security system (e.g., burglar alarms), smart (e.g., networked) garage door opener, smart lock, smart refrigerator, etc., may be used as a sensor to perform selected aspects of the present disclosure.

In various embodiments, control engine 116 may be configured to receive, from bed area sensor 106, one or more signals indicative of activity of a subject detected in bedroom 102. In some embodiments, the one or more signals received from bed area sensor 106 may include a first signal indicative of activity detected in bedroom 102 and a second signal indicative of cessation of activity in bedroom 102 (e.g., following the timeout period mentioned above that is often incorporated into motion sensors). Based on the one or more signals received from bed area sensor 106, such as the aforementioned first and second signals, control engine 116 may identify a first point in time after cessation of the detected activity in bedroom 102 by a predetermined time interval, e.g., 150 seconds. This first point in time may potentially be a beginning of a sleep period and may be referred to herein occasionally as a "sleep begin point in time." Accordingly, control engine 116 may store (e.g., in local memory, or in cloud-based storage) a first indication that signifies a transition of the subject into a state of sleeping of the subject.

In various embodiments, the first indication (and other "indications" mentioned herein) may take the form of a data structure or object that will be referred to herein as a "sleep primitive." In some embodiments, multiple sleep primitives may be stored, each indicative of a potential sleep-related event, such as beginning of a period of sleep and end of a period of sleep. In some embodiments, each sleep primitive may include various values, such as a "Type" (e.g., beginning or end, true or false, etc.), a "Time" (e.g., a timestamp associated with one or more underlying sensor events), a "Space" (e.g., a location at which activity was detected by one or more sensors), etc. As will be described in more detail below, in some embodiments, multiple sleep primitives may be analyzed in the aggregate in order to generate what will be referred to herein as "aggregate" sleep events. Aggregate sleep events may be generated based on two or more sleep primitives and may correspond to conclusions drawn about the subject's sleep behavior. As a simple example, a sleep primitive that indicates a beginning of a sleep period may be combined with a subsequent sleep primitive that indicates an end of a sleep period to form an aggregate sleep event that represents a period of sleep.

Referring back to FIG. 1, at some later point in time, logic 116 may receive, from a second sensor that is adapted to detect activity in (e.g., aimed towards) a second area that is different than bedroom 102 (e.g., hallway sensor 110 and/or bathroom sensor 114), one or more signals indicative of activity in the second area (e.g., hallway 108 and/or bathroom 112). For example, hallway sensor 110 may detect movement in hallway 108. Based on the one or more signals received from the second sensor, control engine 116 may identify a second point in time that is after the sleep begin point in time mentioned previously. This second point of time may provisionally be deemed a wake up time of the subject, and may be referred to herein occasionally as a "sleep end point in time."

When one area is described herein as being "different from" another area, that means the two areas are at least partially spatially distinct. In some embodiments, two areas may be different if respective sensors adapted to detect activity in the areas do not have overlapping fields of view (which implies the two areas are entirely spatially distinct), although this is not required in all cases. In some embodiments, two areas may be different even though respective sensors that detect activity in the areas have partially overlapping fields of view. For example, one sensor may be positioned so that it detects activity in a bed, and another sensor may detect activity in another part of the bedroom, such as near the bedroom door. If the bed is sufficiently near the bedroom door, the two sensors may have at least partially overlapping fields of view. Nonetheless, the bed and the area near the door may be considered spatially distinct. On the other hand, if two sensors have largely overlapping fields of view, say, greater than 70%, then in some embodiments the respective areas monitored by the sensors may not be considered different (although this is not required in all cases) because the two sensors are likely to generate too much crosstalk. Put another way, in some embodiments, two areas are considered different if respective sensors monitoring the areas will not generate crosstalk, or at least will not generate enough crosstalk to impair implementation of techniques described herein or to corrupt conclusions drawn using techniques described herein.

As noted in the background, if another organism such as a visitor or pet is present in the subject's residence, activity by that other organism may trigger a sensor outside of bedroom 102 to raise a spurious signal, even if the subject remains asleep in bedroom 102. Accordingly, control engine 116 may be configured to perform various analysis on signals it receives from sensors to distinguish legitimate sensor events caused by a subject getting out of bed from spurious sensor events caused by another organism in the building. For example, in some embodiments, control engine 116 may determine whether bed area sensor 106 provided any signals indicative of activity detected in bedroom 102 within a particular predetermined time interval (e.g., within thirty seconds or one minute prior) immediately preceding the second point in time associated with the activity detected by the other sensor (i.e. a sensor outside of bedroom 102).

Intuitively, before the presumed-to-be-sleeping subject can create activity that is detected outside of bedroom 102, the subject must first undergo motion to get out of bed and/or leave bedroom 102. The motion of getting out of bed 104/leaving bedroom 102 would be captured by bed area sensor 106. Accordingly, in various embodiments, if control engine 116 receives one or more signals indicative of activity detected by bed area sensor 106 within the predetermined time interval immediately preceding receipt of the outside sensor signal, then control engine 116 may store (e.g., in local and/or cloud-based storage) a second indication (e.g., a sleep primitive) that signifies a transition of the subject into an awake state. On the other hand, if no such corroborating activity is detected, then control engine 116 may disregard or otherwise discard the signal received from the other sensor (e.g., 110, 114) as spurious.

Figure 2:
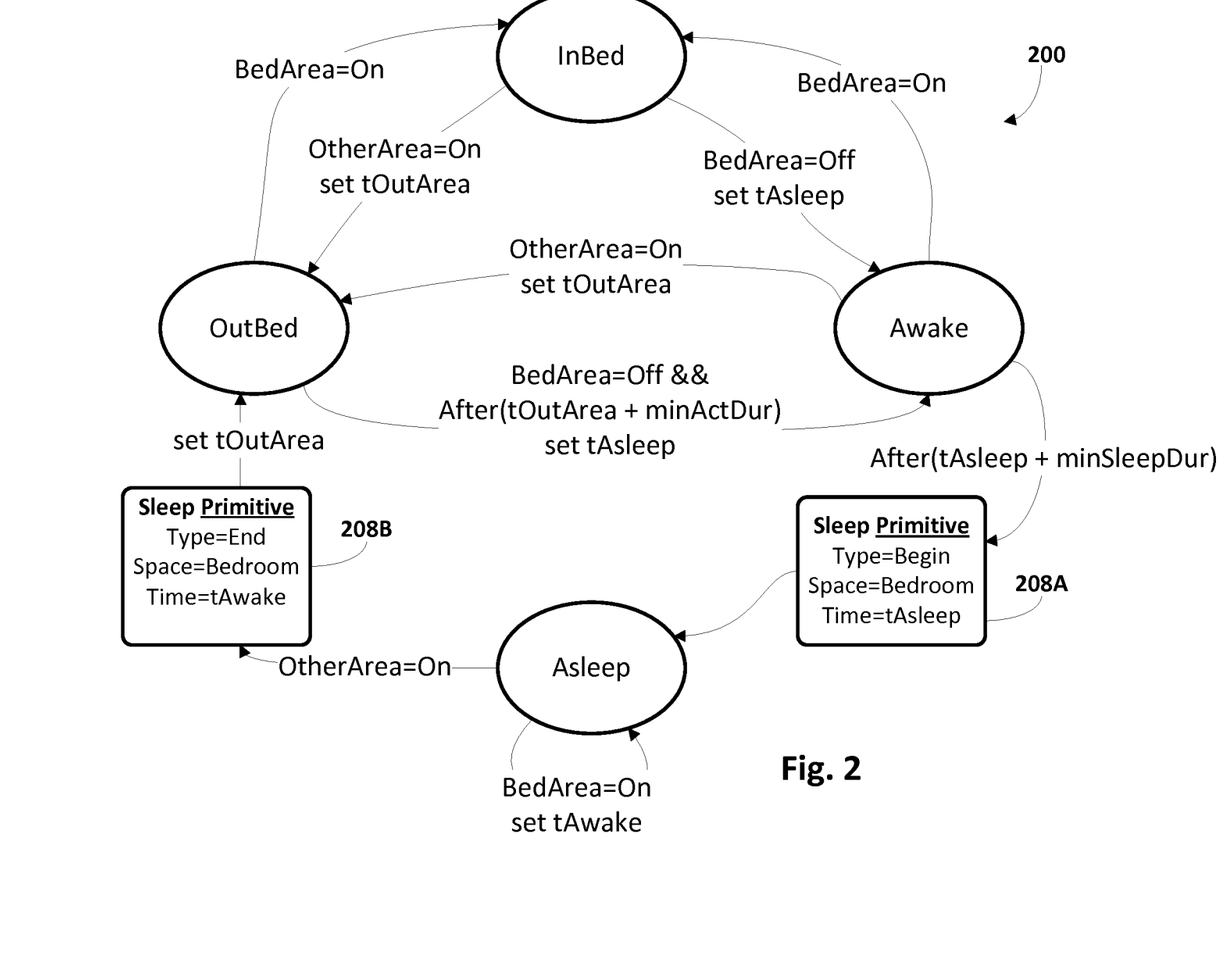
FIG. 2 illustrates one example of a state machine that may be used to detect periods of inactivity of a subject.

FIG. 2 depicts a state machine 200 that corresponds to one example algorithm for detecting periods of inactivity, such as sleep, that may be implemented, for instance, by control engine 116. Four possible states of a subject being monitored are depicted: OutBed (which means the subject is out of bed); InBed (meaning the subject is in bed); Awake (meaning the subject is potentially, but not necessarily, awake), and Asleep. Suppose the state machine 200 is initiated in the OutBed state, and a bed area sensor (e.g., 106) detects activity (BedArea=On). State machine 200 may transition from the OutBed state to the InBed state. Now, suppose the bed area sensor provides an off signal (BedArea=Off). In general, some sensors may be designed to provide an Off signal (e.g., BedArea=Off) at some predetermined timeout period after they no longer detects activity. In some embodiments this predetermined timeout period may be sensor-specific (e.g., set by the manufacturer for, say, one minute, half a minute, ten seconds, etc.) and may or may not be adjustable as desired. Other sensors may provide an Off signal immediately when activity is no longer detected. Whichever the case, the BedArea=Off signal may transition state machine 200 from the InBed state to the Awake State (so-named because absence of movement does not necessarily imply immediate sleep). In some embodiments, a variable tAsleep may be set to a point in time such as a timestamp associated with the BedArea=Off signal.

Next, suppose a predetermined time interval (minSleepDur in FIG. 2) elapses after tAsleep (After(tAsleep+minSleepDur) in FIG. 2). As noted above, minSleepDur may be, for instance, 150 seconds, five minutes, etc. When that occurs, state machine 200 may transition from the Awake state to the Asleep state. During this transition, in some embodiments, a sleep primitive 208A may be generated (e.g., as a data structure, file, database entry, etc.) and stored in (local or cloud-based) memory. In various embodiments, the sleep primitive 208A may include variables such as, for example, a Time with the value set to tAsleep, a Type with a value of "Begin," and a Space with a value of "bedroom" to indicate the location of the event. The Type indicates that this primitive suggests a potential beginning of a sleep period (although in some embodiments sleep primitive 208A may need to be aggregated with other sleep primitive (s) before it is truly considered part of an aggregate sleep event). The Space indicates where the potential sleep event is occurring. While in this example Space may be the bedroom, this is not meant to be limiting. In various, a subject may sleep in other areas, such as on a couch/bed in another room such as a living room, and Space may be set to a value that denotes that actual sleeping location (e.g., bedroom, living room, patio, etc.). More generally, techniques described herein are not limited to tracking sleep behavior in a bedroom, and in fact are able to track sleep behavior in any area of a subject's residence.

While in the Asleep state, the subject may move around in bed without necessarily getting out of bed or even waking up. Nevertheless this movement may be detected by the bed area sensor, triggering it to raise a signal (BedArea=On). In some embodiments, another variable, tAwake, may be set to a timestamp associated with the signal. However, it is not yet assumed that the subject is awake. That only occurs if another sensor in another area detects activity (OtherArea=On). Rather, each time the bed area sensor raises a new BedArea=On signal after having raised a BedArea=Off signal—which could occur every time the subject repositions herself in bed—tAwake is reset (e.g., overwritten) to a new timestamp associated with the latest BedArea=On signal.

However, if the subject truly gets out of bed and then goes to another area, another sensor (e.g., 110, 114) may detect the subject's activity (OtherArea=On). This causes another sleep primitive 208B representing a potential end of sleep to be created, with values similar to the sleep primitive 208A associated with the beginning of sleep except that the Time is set to (the most recently detected instance of) tAwake and the Type is "End." In some embodiments the Space value may be set to the sleeping area and/or the other area in which activity is detected. At the same time, state machine 200 may be transitioned from the Asleep state back to the OutBed State. In some embodiments, a variable tOutArea may be set to a timestamp associated with the just-raised OtherArea=On signal.

There may be instances in which a presumed-sleeping subject gets out of bed and then returns to bed relatively quickly, e.g., to turn off a light in the hallway. Such activity nonetheless may trigger an OutArea=On signal that transitions state machine 200 from the Asleep State to the OutArea state. However, due to the timeout period built into some sensors (described above), the subject may have already returned to bed before the bed area sensor has had a chance to raise a BedArea=Off signal (in some embodiments, it may be expected that BedArea=On signals be followed by BedArea=Off signals, and vice versa). In that event, if the BedArea=Off signal is fired more than a time interval minActDur after tOutArea (After(tOutArea+minActDur) in FIG. 2), state machine 200 may be transitioned from the OutBed state into the Awake state. In various embodiments, minActDur may be selected to be less than or equal to the timeout period associated with the BedArea=Off signal fired by the bed area sensor.

The remaining state transitions in FIG. 2 are relatively straightforward. If a BedArea=On signal is received while state machine 200 is in the Awake state, that suggests the subject is still moving around and has not yet fallen asleep. Accordingly, state machine 200 may simply be transitioned back into the InBed state, and tAsleep may be reset when a new BedArea=Off signal is raised by the bed area sensor. If an OtherArea=On signal is received from a sensor in another area while state machine 200 is in the Awake or InBed states, that suggests the subject left bed before falling asleep. Accordingly, state machine 200 may be transitioned to the OutBed state (and in some cases tOutArea may be set to the corresponding timestamp).

Figure 3:
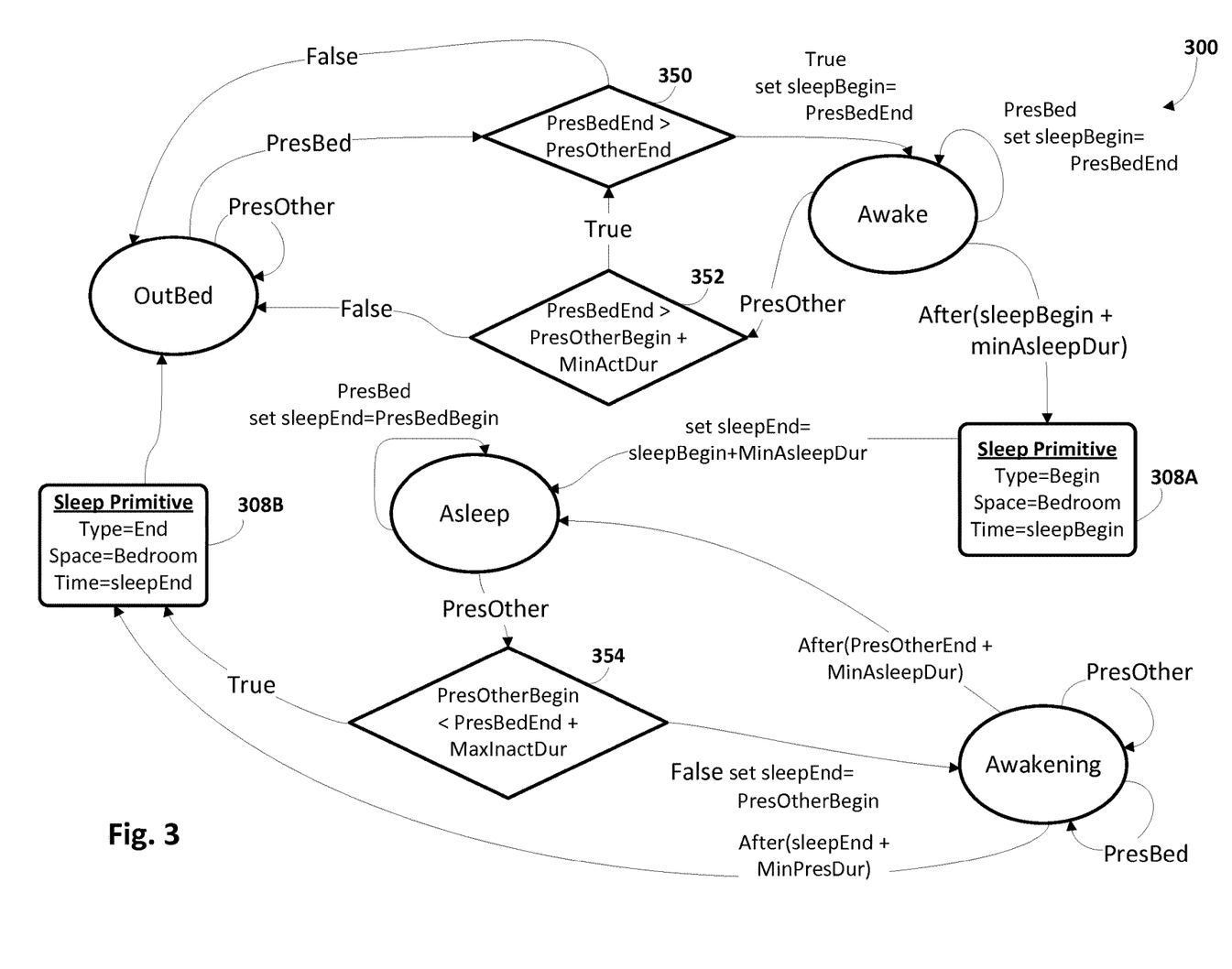
FIG. 3 illustrates another example of a state machine that may be used to detect periods of inactivity of a subject.

FIG. 3 depicts an alternative state machine 300 that may be implemented, e.g., by control engine 116, in order to track periods of inactivity, such as sleep periods of a subject. State machine 300 differs from state machine 200 in a number of ways. To begin, state machine 300 includes additional operations that account for spurious signals from sensors outside of an area being monitored for inactivity (e.g., sleeping). Moreover, transitions between the various states of state machine 300 are triggered by sensor "events" that have beginning and end values. A sensor event beginning value represents a point in time (e.g., a timestamp) when activity is first detected. A sensor event end value represents another point in time (e.g., a timestamp) at which a sensor provides an "Off" signal.

For example, when a bed area sensor (e.g., 106 in FIG. 1) detects activity, it provides what will be referred to in the context of FIG. 3 as a "PresBed" sensor event that includes a PresBedBegin value that may correspond to a timestamp generated at the onset of the detected activity and a PresBedEnd value that corresponds to a timestamp generated with an "Off" signal. In FIG. 3, the so-called "PresOther" sensor event may correspond to a signal raised by a sensor outside of the bed area, such as hallway sensor 110 or bathroom sensor 114 in FIG. 1. Similar to the PresBed event, the PresOther event may also include PresOtherBegin and PresOtherEnd values. Unless otherwise indicated, when a PresBedBegin, PresBedEnd, PresOtherBegin, or PresOtherEnd value is mentioned below, it refers to the value associated with the most recently-raised corresponding sensor event (PresBed or PresOther). In various embodiments, control engine 116 may process sensor events in an order that is dictated by the events' respective Begin values.

Starting from the OutBed state, if a PresBed event is raised, control is passed to a conditional statement 350. Conditional statement 350 tests whether the PresBedEnd value associated with the just-raised PresBed event is temporally after the most recent PresOtherEnd value associated with the most recent PresOther event. Intuitively, conditional statement 350 tests whether the subject was more recently detected in bed than in another area. If the outcome is True, then a sleepBegin variable (similar to the tAsleep variable in FIG. 2) may be set to the PresBedEnd value associated with the just-raised PresBed event. Then, state machine 300 may be transitioned into the Awake state.

While in the Awake state, if a new PresBed event is raised (e.g., bed area sensor 106 detects further activity by the subject in or around the bed), the variable sleepBegin is reset to the new PresBedEnd value associated with the just-raised PresBed event. If a PresOther event is raised, then another conditional statement 352 may be called. Conditional statement 352 tests whether PresBedEnd is temporally after the PresOtherBegin value associated with the just-raised PresOther event, plus a time interval MinActDur (minimum duration of sleeping area activity before going to sleep; e.g., thirty seconds). If the outcome of conditional statement 352 is true, then control may pass back to conditional statement 350 (described above). If the outcome of conditional statement 352 is false, then state machine 300 may be transitioned back into the OutBed state. Back at the Awake state, if no activity is detected anywhere for a time interval minAsleepDur (e.g., 120-150 seconds) following sleepBegin (After(sleepBegin+minAsleepDur)), then a sleep primitive 308A may be generated that is similar to sleep primitive 208A in FIG. 2. State machine 300 may be transitioned into the Asleep state, and a variable sleepEnd may be set by default to a sum of the sleepBegin value and MinAsleepDur.

While in the Asleep state, PresBed events do not cause state machine 300 to transition to a different state. Instead, the sleepEnd variable is merely reset to the PresBedBegin value associated with the most recently-raised PresBed event. Similar to above, intuitively this accounts for movement by the subject in the bed that does not result in the subject leaving the room. However, in the Asleep state, if a PresOther event is raised, then control passes to another conditional statement 354.

Conditional statement 354 tests whether PresOtherBegin temporally precedes PresBedEnd plus a MaxInactDur (i.e. a maximum allowed duration of inactivity between awakening and being out of bed; e.g., 60 seconds). If the outcome of conditional statement 354 is false, then state machine 300 may be transitioned into a so-called "Awakening" state, and the variable sleepEnd may be set to PresOtherBegin. However, if the outcome of conditional statement 354 is True, then a sleep primitive 308B may be generated that is similar to sleep primitive 208B in FIG. 2, and state machine 300 may be transitioned back into the OutBed state.

Back in the Awakening state, PresBed and PresOther events may not themselves necessarily lead to transition to another state of state machine 300. Rather, if a time interval MinSleepDur (e.g., two minutes) passes after PresOtherEnd (After(PresOtherEnd+MinSleepDur) in FIG. 3), then state machine 300 may be transitioned back to the Asleep state. On the other hand, if a time interval MinPresDur (e.g., a minimum duration of activity in other areas outside of the bedroom that implies non-sleep; e.g., four minutes) passes after sleepEnd (which was set to PresOtherBegin when entering the Awakening state, i.e. it is not updated with subsequent PresOther events; in contrast PresOtherEnd is updated by subsequent PresOther events), the sleep primitive 308B may be generated. State machine 300 may then transition back into the OutBed state.

Intuitively, the relationship between conditional statement 354 and the Asleep and Awakening states is designed to detect and discard spurious PresOther events that may be caused, for instance, by a pet or visitor moving around in another area while the subject remains in bed. Suppose it is 3:00 AM and the subject is fast asleep in bed and that no activity has been detected from the subject for two hours (i.e., the last-raised PresBed event set the PresBedEnd value to 1:00 AM). Suppose further that five minutes of activity of a pet is detected in another room (e.g., the pet eats some food, users a litter box, etc.), thereby raising a PresOther event with a PresOtherBegin value of 3:00 AM and a PresOtherEnd value of 3:05 AM. At conditional statement 354, the PresOtherBegin value (3:00 AM) occurs after last PresBedEnd value (1:00 AM) plus MaxInactDur (sixty seconds), or after 1:01 AM. Accordingly, conditional statement 354 returns false, and state machine 300 may be transitioned into the Awakening state (which does not necessarily imply that the subject is awakening, but merely signifies a potential awakening of the subject). If no other PresOther events are raised, after passage of the time interval MinAsleepDur (e.g., two minutes) plus PresOtherEnd (3:05 AM), i.e., at 3:07 AM, state machine 300 may be transitioned back to the Asleep state. Thus, it can be seen that conditional statement 354 effectively serves to determine whether bed area sensor 106 detected activity in bedroom 102 within a time interval immediately preceding PresOtherBegin.

As noted above, in some embodiments, sleep primitives (e.g., 208A, 208B, 308A, 308B) may be analyzed in combination to generate so-called "aggregate" events. An aggregation routine may evaluate a temporal sequence of generated sleep primitives to identify genuine periods of inactivity such as sleep. For example, the aggregation routine may wait for a sleep primitive having a Type of "Begin." If an immediately prior sleep primitive also had a Type of "Begin," then the current sleep primitive (or the prior sleep primitive) may be discarded, for example. Intuitively, when movement is detected in the bedroom but no movement is thereafter detected by non-bed area sensors, the implication is that the subject merely moved around in bed, and sleep was not necessarily interrupted. The variable sleepBegin may be set to the Time of the (non-discarded) Begin-Type sleep primitive. If this point in time is within a maximum duration (e.g., 150 seconds) of the sleepEnd of a last-stored aggregate event, the primitive event may be aggregated with the last-stored aggregate event. However, in some embodiments, the primitive events may not be aggregated, e.g., if a caregiver wants to be informed on bed exits, e.g., for using the toilet, including the number of and/or duration of the bed exits.

If a current sleep primitive has a Type of "End," then it may be tested to be after a minimum duration (e.g., a half hour) since the last sleep primitive have a Type of "Begin." This minimum duration effectively establishes a minimum duration of sleeping. If the minimum duration is surpassed, an aggregate event may be created to indicate a sleep period. The beginning of the aggregate sleep period may be indicated by the Time associated with the last (non-discarded) sleep primitive having a Type of "Begin." The end of the aggregate sleep period may be indicated by the Time associated with the current sleep primitive having a Type of "End." In the event the current sleep primitive is aggregated with a prior aggregate event as described above, no new aggregate event is generated/stored. Instead, the prior aggregate event may be updated to have its ending time set to the Time of the current Type-End sleep primitive. In some embodiments, the number of aggregate events and/or sleep primitives that are aggregated into a final aggregate are tracked, and may be used, for instance, to gauge sleep efficacy.

Figure 4:
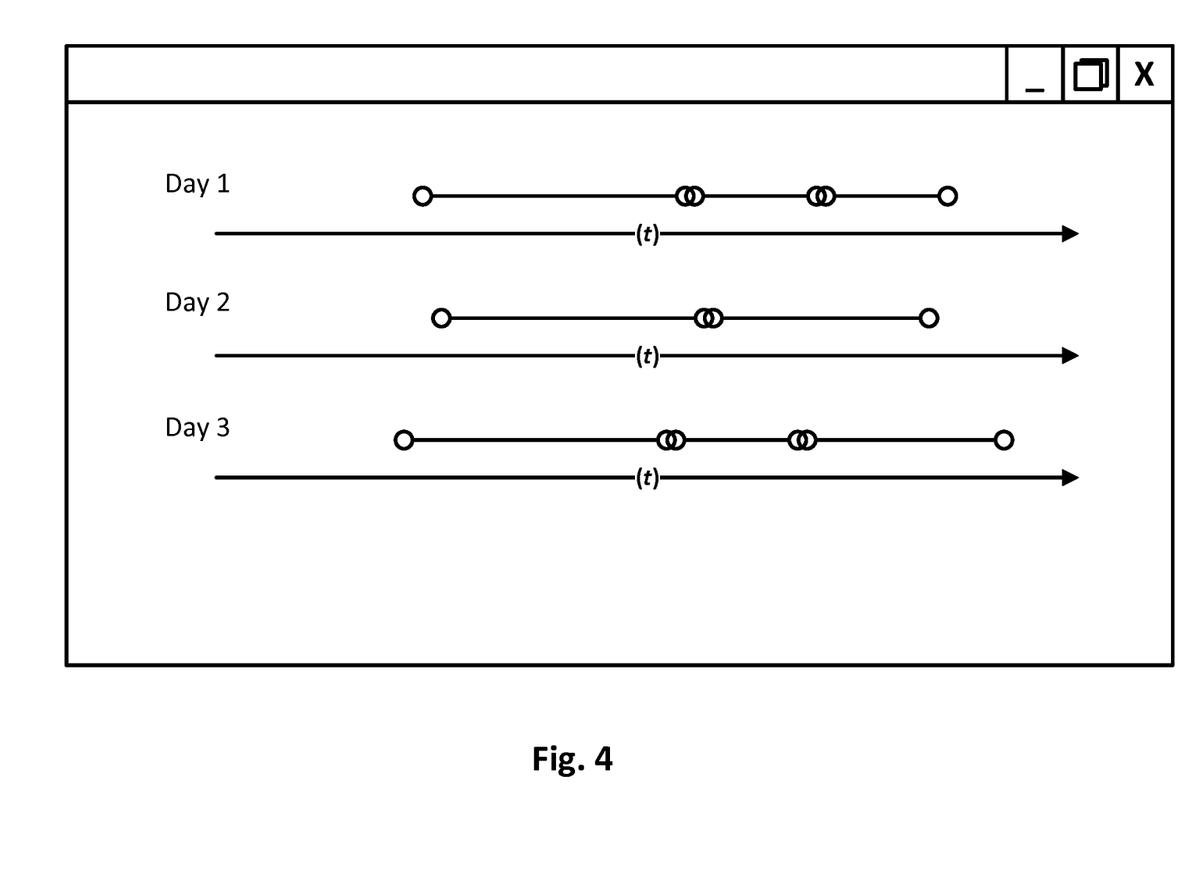
FIG. 4 depicts one example of a graphical user interface that displays periods of detected inactivity (e.g., sleep) using techniques described herein.

FIG. 4 depicts one example of a graphical user interface that depicts periods of sleep represented by aggregate sleep periods that were detected over three days. The horizontal axes represent time (the axis is not to scale and is not intended to represent a 24-hour period but instead simply represents a general period during each day during which a subject sleeps). As shown by the plots and circular endpoints, in day 1, the subject slept for a relatively long first period, got out of bed briefly before returning to bed for a second slightly shorter period of sleep, and then left bed once more before getting back into bed for a third period of sleep. In day 2 the subject went to sleep somewhat later than in day 1 but only left bed once between periods of sleep. In day three the subject exhibited sleeping patterns similar to those of day 1, except that the subject collectively slept longer.

Figure 5:
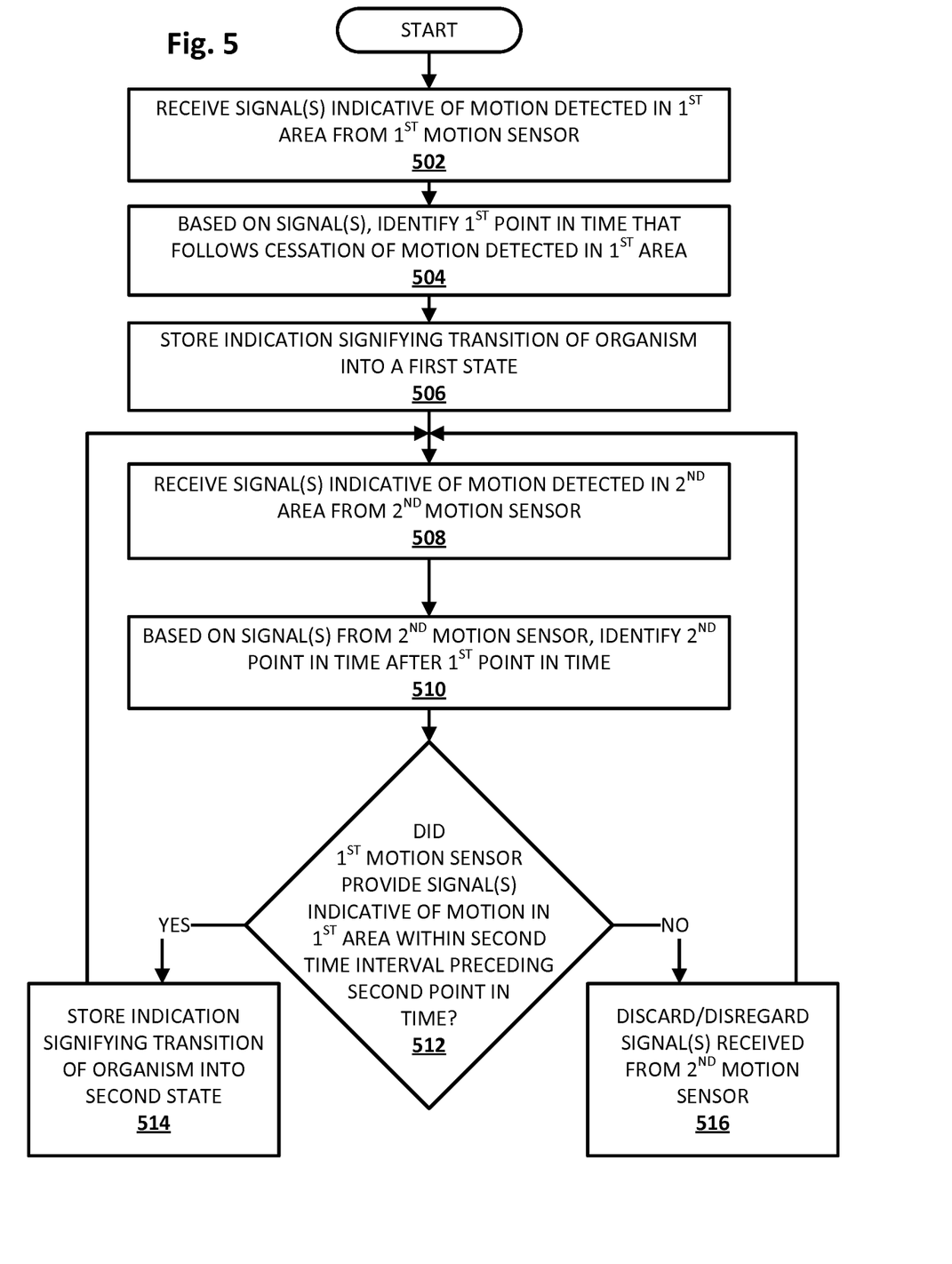
FIG. 5 depicts an example method for practicing selected aspects of the present disclosure, in accordance with various embodiments.

FIG. 5 depicts an example method 500 for practicing selected aspects of the present disclosure, in accordance with various embodiments. For convenience, the operations of the flow chart are described with reference to an apparatus that performs the operations. This apparatus may include various components of various computer systems, including control engine 116 and/or computing systems remote from control engine 116. Moreover, while operations of method 500 are shown in a particular order, this is not meant to be limiting. One or more operations may be reordered, omitted or added.

At block 502, the apparatus receives, from a first sensor such as bed area sensor 106, a first set of one or more signals indicative of activity detected in a first area (e.g., bedroom 102). In some embodiments, separate signals may be received at the onset and at/after cessation of the detected activity. Additionally or alternatively, in some embodiments, a single and/or continuous signal may be received that is interpreted as an event (e.g., PresBed, PresOther described with regard to FIG. 3) having a beginning (e.g., PresBed-Begin, PresOtherBegin) and an end (e.g., PresBedEnd, PresOtherEnd).

At block 504, the apparatus may identify a point in time after cessation of the activity detected in the first by some predetermined time interval. For example, in state machine 200 of FIG. 2, while in the Awake state, if a time interval minSleepDur passed after tAsleep, it was presumed that the subject was, in fact, asleep. Similarly, in state machine 300 of FIG. 3, while in the Awake state, if a time interval minAsleepDur passed after sleepBegin, it was presumed that the subject was, in fact, asleep.

At block 506, based on the identification of block 504, the apparatus may store a first indication that signifies a transition of the subject into a first state at the first point in time. For example, in FIGS. 2 and 3, sleep primitives 208A, 308A were stored with Types of "Begin" to signify potential transition of the subject into a state of Asleep.

At block 508, the apparatus may receive a second set of one or more signals from a second sensor adapted to detect activity in a second area that is different than the first area. For example, hallway sensor 110 is adapted to detect activity in hallway 108 in FIG. 1. Bathroom sensor 114 is adapted to detect activity in bathroom 112. These signal(s) may be indicative of activity detected in the second area (e.g., hallway 108, bathroom 112). At block 510, based on the signals received from the second sensor at block 508, the apparatus may identify a second point of time after the first point in time identified at block 504. For example, the second point in time may be the onset of the detected activity outside of the bedroom (e.g., PresOtherBegin).

At block 512, the apparatus may determine whether the first sensor provided any signals indicative of activity detected in the first area within a second time interval immediately preceding the second point in time. For example, did bed area sensor 106 provide any signals indicative of activity detected in bedroom 102 immediately prior to activity detected in hallway 108 by hallway sensor 110. Lack of such activity indicates that the out-of-bedroom activity was caused by an organism other than the subject. If the answer at block 512 is yes, then method 500 may proceed to block 514; otherwise method 500 may proceed to block 516.

At block 514, the apparatus may store a second indication that signifies a transition of the subject into a second state. For example, the apparatus may generate and/or store another sleep primitive, such as 208B or 308B, with a Type of "End" that signifies a transition of the subject to being awake and/or out of the bedroom. On the other hand, at block 516, the apparatus may disregard or discard the one or more signals received from the second sensor.

Techniques described herein are not limited to detected periods of sleep. More generally, the techniques described herein are capable of removing spurious events from monitoring of any activities of a subject. The general principle is that an event in one space (e.g., room) should be preceded by event in the same space or otherwise in space room shortly before. If not, the event is considered spurious and a candidate to be discarded. However, in some embodiments, if the presence in the new space is sustained the event is kept, e.g., to mitigate against a missed presence in the previous space.

The following algorithm comprises one example of how spurious events may be discarded (e.g., filtered out), in accordance with various embodiments. The following parameters may be used for this algorithm:

SP_transGap: max time (e.g., in seconds) there is no presence between leaving one space and being present in next space. In some embodiments this may be set to 150 seconds.

SP_spurDur: max duration (e.g., in seconds) of presence to be considered spurious. In some embodiments this may be set to 45 seconds.

SP_spurGap: gap (e.g., in seconds) at which presence span is split in cluster over which to determine spurious. In some embodiments this may be set to 240 seconds.

SP_spurDensity: max density of presence in span to be considered spurious (e.g., 0 . . . 1). In some embodiments this may be set to 0.01.

The following is pseudocode for the algorithm:

```
Init
    presSpan: list of triples:
        'spaceID': name of space [string]
        'ev': Presence EventP that are potentially spurious [list]
        'spurious': EventP in 'ev' are spurious [Boolean]
    Pres1 = [ ]
    curSpan = current space [presSpan]
    lastSpace = last non-spurious space [string]
for ev0 in Pres0:
    if ev0 is in same space as curSpan:
        add 'ev0' to curSpan's 'ev' list
    else:
        curSpan is spurious, when
            Boolean spurious of curSpan is True
            The function isSpurious(curSpan) returns True //defined below
            Space of curSpan is not same as lastSpace
        if curSpan is not spurious:
            lastSpace = curSpan['spaceID']
        Assign curSpan to ev0['SPACE']
        If there is another sp in presSpan, such that
            sp is not spurious, and
            ev0['BEGIN'] is within SP_transGap from sp['END']
        then: output curSpan (its list 'ev' holds non-spurious events)
        else: output all 'ev' lists from other sp in presSpan that are labeled
    spurious==False
        add 'ev0' to curSpan's 'ev' list
```

```
            for all other sp in presSpan that are:
                sp is spurious, and
                ev0['BEGIN'] is after SP_transGap from sp['END']
            empty their 'ev' list
The function isSpurious(span0):
    Returns True when
        Total duration of 'ev' list is below 'SP_spurDur', or
        Density of presence over total duration is below threshold
    Density of presence is determined per so-called cluster
    Cluster is subset of 'ev' list where END and BEGIN time of boundary elements
        are SP_spurGap apart
The span0 is spurious when for all clusters
    Cluster duration is below 'SP_spurDur', or
    Fraction of total duration of active presence within cluster relative to cluster
        duration is less than 'SP_spurDensity'
            Total duration of active presence is sum of durations of events in
                (cluster's) 'ev' list
```

The apparatus herein disclosed may further comprise the first sensor 106 and the second sensor 110, thereby forming an embodiment of a system (not shown) in accordance with the present invention. The system may comprise additional sensors, e.g. sensor 114, which can be located in a plurality of areas, thereby providing a plurality of field of views for enabling the drawing of conclusions on sleeping pattern and/or behavior of the subject.

A system in accordance with the present invention is not limited by the number of sensors, which can be 2, 3, 4, 5, 10, insofar as the effect(s) herein mentioned which may be derived from the sensor signals as processed, for instance by the processor comprised in the apparatus, are achieved.

Figure 6:
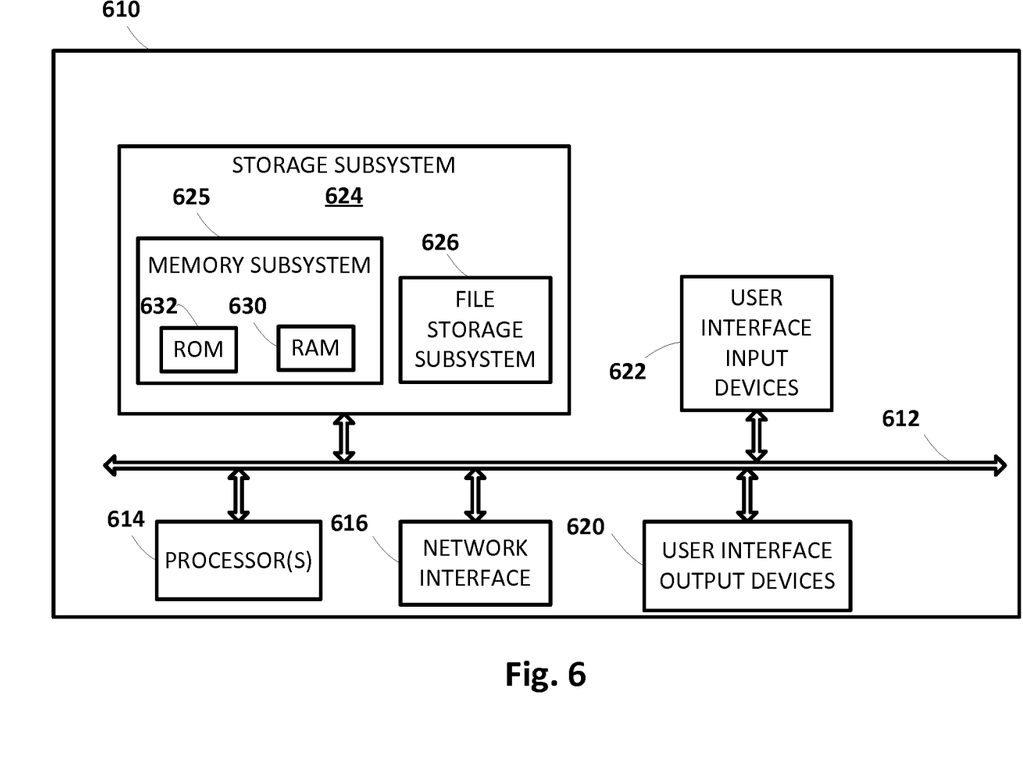
FIG. 6 depicts an example computing system architecture.

FIG. 6 is a block diagram of an example computer system 610. Computer system 610 typically includes at least one processor 614 which communicates with a number of peripheral devices via bus subsystem 612. These peripheral devices may include a storage subsystem 624, including, for example, a memory subsystem 625 and a file storage subsystem 626, user interface output devices 620, user interface input devices 622, and a network interface subsystem 616. The input and output devices allow user interaction with computer system 610. Network interface subsystem 616 provides an interface to outside networks and is coupled to corresponding interface devices in other computer systems.

User interface input devices 622 may include a keyboard, pointing devices such as a mouse, trackball, touchpad, or graphics tablet, a scanner, a touchscreen incorporated into the display, audio input devices such as voice recognition systems, microphones, and/or other types of input devices. In general, use of the term "input device" is intended to include all possible types of devices and ways to input information into computer system 610 or onto a communication network.

User interface output devices 620 may include a display subsystem, a printer, a fax machine, or non-visual displays such as audio output devices. The display subsystem may include a cathode ray tube (CRT), a flat-panel device such as a liquid crystal display (LCD), a projection device, or some other mechanism for creating a visible image. The display subsystem may also provide non-visual display such as via audio output devices. In general, use of the term "output device" is intended to include all possible types of devices and ways to output information from computer system 610 to the user or to another machine or computer system.

Storage subsystem 624 stores programming and data constructs that provide the functionality of some or all of the modules described herein. For example, the storage subsystem 624 may include the logic to perform selected aspects of method 500, and/or to implement one or more aspects of control engine 116. Memory 625 used in the storage subsystem 624 can include a number of memories including a main random access memory (RAM) 630 for storage of instructions and data during program execution and a read only memory (ROM) 632 in which fixed instructions are stored. A file storage subsystem 626 can provide persistent storage for program and data files, and may include a hard disk drive, a CD-ROM drive, an optical drive, or removable media cartridges. Modules implementing the functionality of certain implementations may be stored by file storage subsystem 626 in the storage subsystem 624, or in other machines accessible by the processor(s) 614.

Bus subsystem 612 provides a mechanism for letting the various components and subsystems of computer system 610 communicate with each other as intended. Although bus subsystem 612 is shown schematically as a single bus, alternative implementations of the bus subsystem may use multiple busses.

Computer system 610 can be of varying types including a workstation, server, computing cluster, blade server, server farm, smart phone, smart watch, smart glasses, set top box, tablet computer, laptop, or any other data processing system or computing device. Due to the ever-changing nature of computers and networks, the description of computer system 610 depicted in FIG. 6 is intended only as a specific example for purposes of illustrating some implementations. Many other configurations of computer system 610 are possible having more or fewer components than the computer system depicted in FIG. 6.

Various aspects of the present disclosure may be implemented in a computer program product, which may be a collection of computer program instructions stored on a computer readable storage device which may be executed by a computer. The computer program instructions may be in any interpretable or executable code mechanism, including but not limited to scripts, interpretable programs, dynamic link libraries (DLLs) or Java classes. The instructions can be provided as complete executable programs, partial executable programs, as modifications to existing programs (e.g. updates) or extensions for existing programs (e.g. plugins). Moreover, parts of the processing of the present disclosure may be distributed over multiple computers or processors.

As discussed above, the processing unit, for instance a controller, may implement various methods described herein. The controller can be implemented in numerous ways, with software and/or hardware, to perform the various functions described herein. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform at the required functions. Various storage media may be fixed within a processor or controller or may be transportable, such that the one or more programs stored thereon can be loaded into a processor or controller. While the invention has been illustrated and described in detail in the drawings and foregoing description, such illustration and description are to be considered illustrative or exemplary and not restrictive; the invention is not limited to the disclosed embodiments.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be understood that certain expressions and reference signs used in the claims pursuant to Rule 6.2(b) of the Patent Cooperation Treaty ("PCT") do not limit the scope.

What is claimed is:

1. A computer-implemented method determining one or more period of inactivity of a subject, the computer-implemented method comprising: receiving, by logic communicatively coupled with a first sensor that is detecting activity in a first area, the first area comprising a sleeping area, a first set of one or more signals indicative of detected activity of the subject within the first area; identifying, by the logic, based on the first set of one or more signals received from the first sensor, a first point in time after cessation of the detected activity within the first area by a predetermined time interval; storing, by the logic based on the identifying, a first indication that signifies a transition of the subject into a first state at the first point in time, wherein the first state is a sleep state; receiving, by the logic communicatively coupled with a second sensor that is detecting activity in a second area that is different than the first area, a second set of one or more signals indicative of activity within the second area; identifying, by the logic, based on the second set of one or more signals received from the second sensor, a second point in time that is after the first point in time; determining, by the logic, whether the first sensor provided any signals indicative of activity detected in the first area within a second time interval immediately preceding the second point in time: if the first sensor provided any signals indicative of activity detected in the first area within the second time interval immediately preceding the second point in time, storing, by the logic, a second indication that signifies a transition of the subject into a second state, wherein the second state is an awake state; and if the first sensor did not provide any signals indicative of activity detected in the first area within the second time interval immediately preceding the second point in time, refraining from storing, by the logic, the second indication that signifies a transition of the subject into the second state.

2. The computer-implemented method of claim 1, wherein the receiving of one or more signals indicative of detected activity of the subject within the first area comprises receiving a signal from at least one of a passive infrared sensor, a light sensor, a movement sensor, a pressure sensor, a tactile sensor, or a door opening sensor.

3. The computer-implemented method of claim 1, wherein the one or more signals received from the first sensor include a first signal indicative of motion detected in the first area and a second signal indicative of cessation of motion in the first area.

4. The computer-implemented method of claim 1, wherein the receiving of one or more signals indicative of activity within the second area comprises receiving a signal from a sensor integral with a household appliance.

5. The computer-implemented method of claim 1, wherein the refraining includes disregarding or discarding, by the logic, the one or more signals received from the second sensor.

6. The computer-implemented method of claim 1, wherein the receiving of one or more signals indicative of activity within the second area comprises receiving a signal from a sensor integral with a heating ventilation and air conditioning ("HVAC") appliance.

7. The computer-implemented method of claim 1, wherein the receiving of one or more signals indicative of activity within the second area comprises receiving a signal from a sensor integral with a luminaire.

8. A computer program product comprising a computer readable medium having computer readable code embodied therein, the computer readable code being configured such that, on execution by a suitable computer or processor, the computer or processor is caused to perform the method of claim 1.

9. An apparatus for determining one or more period of inactivity of a subject, the apparatus comprising a processor configured to:
receive a first set of one or more signals indicative of detected activity of a subject in a first area, the first area comprising a sleeping area;
identify, based on the first set of one or more signals, a first point in time after cessation of the detected activity in the first area by a predetermined time interval;
store, based on the identification, a first indication that signifies a transition of the subject into a first state, wherein the first state is a sleep state;
receive a second set of, one or more signals indicative of activity in a second area (108, 102) that is different than the first area;
identify, based on the second set of one or more signals, a second point in time that is after the first point in time;
determine whether the first set of signals provided any signals indicative of activity detected in the first area within a second time interval immediately preceding the second point in time;
if the first set of signals provided any signals indicative of activity detected in the first area within the second time interval immediately preceding the second point in time, store a second indication that signifies a transition of the subject into a second state, wherein the second state is an awake state; and
if the first set of signals did not provide any signals indicative of activity detected in the first area within the second time interval immediately preceding the second point in time, refrain from storing the second indication that signifies a transition of the subject into a second state.

10. A system for determining one or more periods of inactivity of a subject, the system comprising: a first sensor detecting activity in a first area, the first area comprising a sleeping area, and generate a first set of one or more signals indicative of detected activity of a subject within the first area; a second sensor detecting activity in a second area that is different than the first area, and to generate a second set of one or more signals indicative of activity within the second area; a processor communicatively coupled to the first sensor and the second sensor, the processor being configured to: identify, based on the first set of one or more signals received from the first sensor, a first point in time after cessation of the detected activity in the first area by a predetermined time interval; store, based on the identification, a first indication that signifies a transition of the subject into a first state, wherein the first state is a sleep state; identify, based on the second set of one or more signals received from the second sensor, a second point in time that is after the first point in time; determine whether the first sensor provided any signals indicative of activity detected in the first area within a second time interval immediately preceding the second point in time: if the first sensor provided any signals indicative of activity detected in the first area within the second time interval immediately preceding the second point in time, store a second indication that signifies a transition of the subject into a second state, wherein the second state is an awake state; and if the first sensor did not provide any signals indicative of activity detected in the first area within the second time interval immediately preceding the second point in time, refrain from storing the second indication that signifies a transition of the subject into a second state.

11. The system of claim 10, wherein the first sensor comprises at least one of a passive infrared sensor, a light sensor, a movement sensor, a pressure sensor, a tactile sensor, or a door opening sensor.

12. The system of claim 10, wherein the first set of one or more signals received from the first sensor includes a first signal indicative of motion detected in the first area and a second signal indicative of cessation of motion in the first area.

13. The system of claim 10, wherein the second sensor is integral with a household appliance.

14. The system of claim 10, wherein the second sensor is integral with a heating ventilation and air conditioning ("HVAC") appliance.

15. The system of claim 10, wherein the second sensor is integral with a luminaire.

* * * * *